United States Patent [19]
Mawhirt et al.

[11] Patent Number: 5,851,215
[45] Date of Patent: *Dec. 22, 1998

[54] LOW COST DISPOSABLE LANCET

[75] Inventors: James A. Mawhirt, Brooklyn, N.Y.;
Anthony F. Kuklo, Jr., Bridgewater, N.J.; Donald Foggia, Ocean, N.J.;
Donald W. Allen, Point Pleasant, N.J.

[73] Assignee: International Technidyne Corporation, Edison, N.J.

[*] Notice: The term of this patent shall not extend beyond the expiration date of Pat. No. 5,630,828.

[21] Appl. No.: 718,773

[22] Filed: Sep. 24, 1996

[51] Int. Cl.$^6$ ................................................. A61B 17/14
[52] U.S. Cl. ......................................... 606/181; 128/770
[58] Field of Search ................................... 606/181, 182, 606/183, 187, 188; 128/770, 771

[56] References Cited

U.S. PATENT DOCUMENTS

| | | |
|---|---|---|
| 3,760,809 | 9/1973 | Campbell, Jr. . |
| 4,553,541 | 11/1985 | Burns . |
| 4,983,178 | 1/1991 | Schnell ..................................... 606/181 |
| 5,133,730 | 7/1992 | Biro . |
| 5,212,879 | 5/1993 | Biro . |
| 5,395,388 | 3/1995 | Schraga . |
| 5,584,846 | 12/1996 | Mawhirt et al. ........................ 606/181 |
| 5,630,828 | 5/1997 | Mawhirt et al. ........................ 128/770 |

Primary Examiner—Michael Buiz
Assistant Examiner—Kevin Truong
Attorney, Agent, or Firm—Plevy & Associates

[57] ABSTRACT

A low cost safety lancet device for creating a skin incision. The lancet contains a unitarily formed plastic body, thereby making the lancet device easy to manufacture at a low cost. The lancet device includes a blade beam having a cutting blade disposed at one end for generating an incision in a patient's skin. The blade beam is pivotally coupled within the device, engages a beam keeper arm in a first position and disengages the beam keeper arm in a second position. Upon activation of the device, the blade beam member resiliently deflects in a first direction as the beam keeper arm moves from the first position to the second position thereby causing a buildup of a biasing force in the beam member. When the blade beam disengages the beam keeper arm in the second position, the biasing force built up in the beam member causes the beam member to pivot, thereby accelerating the cutting blade through an aperture in the lancet device to incise the user's skin. The acceleration of the blade beam and cutting blade resiliently deflects the blade beam into a second direction, building up a second biasing force which causes the blade beam to return to a non-deflected position thereby withdrawing the cutting blade from the user's skin and back through the aperture.

23 Claims, 5 Drawing Sheets

LOW COST DISPOSABLE LANCET

RELATED APPLICATIONS

International Technidyne Corporation, the assignee herein, is record owner of U.S. patent application Ser. No. 08/633,625 entitled LOW COST DISPOSABLE LANCET filed by James A. Mawhirt et al. on Apr. 17, 1996; U.S. patent application Ser. No. 08/465,686 entitled SELF ACTIVATED FINGER LANCET filed by James Mawhirt et al. on Jun. 6, 1995; and U.S. patent application Ser. No. 08/549,173 entitled LOW COST DISPOSABLE LANCET filed by James Mawhirt et al. on Oct. 27, 1995.

FIELD OF THE INVENTION

The present invention relates generally to blood drop generator devices and more particularly to a blood drop generator device having an improved lancet triggering mechanism that is relatively inexpensive and simple to manufacture, assemble and use.

BACKGROUND OF THE INVENTION

Blood drop generation devices provide blood samples which are used in performing various blood tests for preventative medicine and medical diagnosis. Such devices operate by creating a small puncture or incision in the skin of the fingertip or other area of the body such as the foot, arm, or leg.

Since most blood drop generation devices employ a lancet-like structure for puncturing or incising the skin, blood drop generation devices are often referred to as lancet devices. Many prior art lancet devices employ spring loaded cutting blades which are enclosed within a casing or housing. These devices are operated by placing the housing of the device against the skin and triggering the spring loaded cutting blade in the device. The potential energy stored within the spring accelerates the blade through an aperture in the housing and creates a uniform puncture or incision in the skin. The structural configuration of these devices enable the puncture or incision in the skin to be made in a controlled manner in terms of location, size, depth, and sterility. Since the blade is concealed within the housing, the patient is unable to view the blade prior to, or during the puncturing of the skin which reduces the patient's anxiety.

Many of these prior art lancet devices are marketed as "safety" lancet devices because they include means for retracting the blade back into the housing after the puncture or incision has been made. Such safety lancet devices advantageously reduce the probability of a disease being spread through contact with the used blade of the device. This is an important feature since, deadly viruses such as AIDS and Hepatitis can spread from accidental punctures obtained from lancets used previously on an infected patient.

As stated above, the structural configuration of the lancet devices enable the devices to puncture or incise the skin in a controlled manner in terms of location, size and depth. This is accomplished in the prior art by designing the lancet to move in a plunging cutting motion where the cutting blade moves perpendicular to the skin. This produces an incision which substantially matches the size of the cutting blade. Such lancets are exemplified by U.S. Pat. No. 5,133,730 issued on Jul. 28, 1992 to Biro, entitled DISPOSABLE RETRACTABLE FINGER STICK DEVICE AND METHOD FOR MAKING THE SAME and assigned to International Technidyne Corporation the assignee herein. In the Biro patent, a sharp blade is provided on a spring biased pivot arm which moves the blade out through an orifice in the lancet housing and then retracts the blade back into the housing. Although the blade is positioned on a pivot arm, the blade is directed perpendicularly into the surface of the skin. The shape of the blade helps the blade enter the skin and make the needed incision. Other lancet devices that create plunge-type cuts are exemplified in U.S. Pat. No. 3,760,809 to Campbell, Jr. entitled SURGICAL LANCET HAVING CASING and U.S. Pat. No. 5,395,388 to Schraga, entitled SINGLE UNIT LANCET DEVICE.

In order to encourage the disposability of the lancet devices, it is necessary to market such devices at an appropriately low price. Accordingly, the manufacturers of the lancet devices must be able to manufacture the lancet devices to an acceptably low cost in order to make money. This has resulted in the development of lancet designs with only two or three separate parts. Such designs generally employ a cutting blade held by a complex molded structure that both advances and retracts the blade. Examples of this type of lancet device design are shown in U.S. Pat. No. 4,553,541, entitled AUTOMATIC RETRACTABLE LANCET ASSEMBLY, to Burns, and U.S. Pat. No. 5,212,879, entitled METHOD FOR MANUFACTURING A DISPOSABLE-RETRACTABLE FINGER STICK DEVICE to Biro et al., which is assigned to International Technidyne Corp., the assignee herein. Although such lancet devices have fewer parts than earlier designs, they still tend to be relatively expensive to produce due to the complex nature of the tooling which requires frequent cleaning and maintenance, and the close tolerance nature of the parts. Accordingly, a substantially high percentage of rejected parts and significant downtime are associated with these prior art designs. Hence the cost of such lancet devices remain unacceptably high.

In many prior art lancet devices, expensive metal springs are utilized for various purposes. For example, in some existing lancet designs, the metal springs form a portion of the cutting blade. In other existing lancet designs, the cutting blade is separate from and driven by the spring. In either design, the springs add significantly to the overall cost of the lancet device as well to the complexity of assembling the lancet device with the spring in its compressed, ready-to-use orientation.

Accordingly there is need for an improved disposable safety lancet which is relatively inexpensive to manufacture, assemble and use.

SUMMARY OF THE INVENTION

A unitarily formed safety lancet device, comprising a first arm member, a second arm member slidably engaging along the first arm from a first position to a second position when the lancet device is compressed to operate by a user. A pivotally coupled beam member having a cutting blade disposed at an end thereof is also provided. The end of the beam member engages the second arm member in the first position and disengages the second arm in the second position, wherein the beam member resiliently deflects in a first direction as the second arm moves from the first position to the second position. This causes a buildup of a biasing force in the beam member, the biasing force causing the beam member to accelerate the cutting blade through an aperture in the lancet device to incise the user's skin when the beam member disengages the second arm in the second position.

BRIEF DESCRIPTION OF THE DRAWINGS

For a detailed understanding of the present invention, reference should be made to the following detailed description taken in conjunction with the accompanying drawings wherein.

DETAILED DESCRIPTION OF THE DRAWINGS

Figure 1:
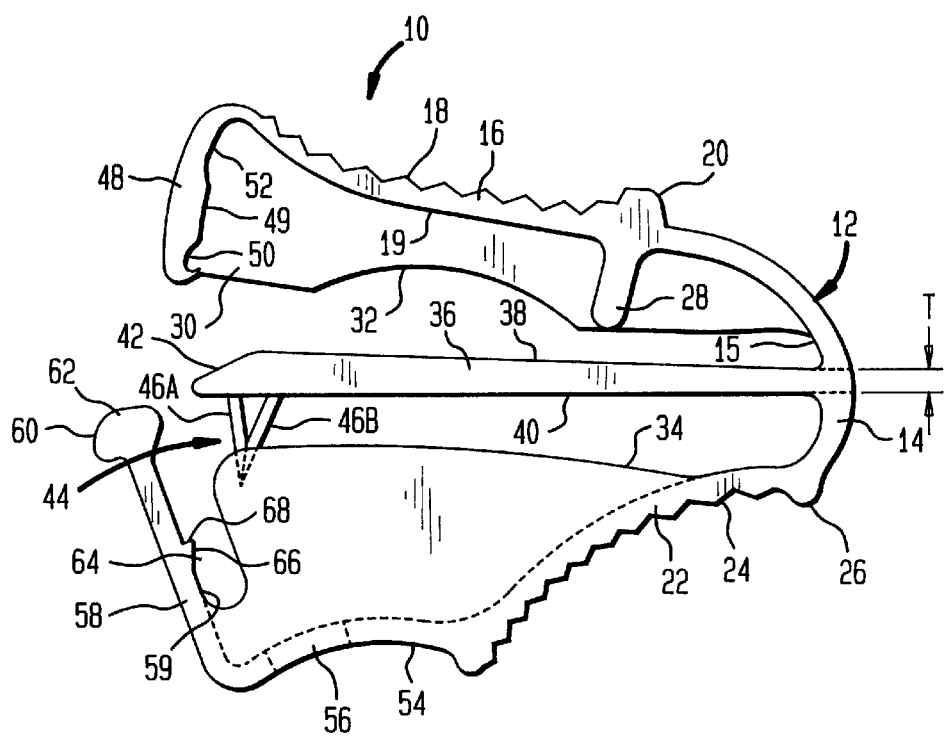
FIG. 1 is an as molded perspective view of the lancet device of the present invention.

Referring to FIG. 1, the lancet device 10 of the present invention is shown in an "as molded" condition. The lancet device 10 essentially comprises two separately fabricated parts, a molded plastic body 12 and a metallic cutting blade 44. Alternatively, the lancet device 10 can be comprised of a single unitary plastic part molded from a single plastic material, two co-injected plastic materials or two stage injected plastic materials, where the cutting blade 44 is molded from the same or one of the two co-injected or two stage injected plastic materials and the plastic body 12 is molded from the same or the other of the two co-injected or two stage injected plastic materials.

In any case, the plastic body 12 includes a resiliently deflectable spring loop 14 having an arcuate-shaped thumb rest 16 extending from one end thereof, an arcuate-shaped second person user assist finger rest 22 extending from the other end thereof, and a resiliently deflectable blade beam 36 pivotally extending from the inner surface 15 thereof. Depending from a free end of the thumb rest is a detent arm 48. The inner surface 49 of the detent arm 48 includes a hook-like detent notch 50 disposed adjacent to the free end thereof, and a beam keeper release notch 52 disposed adjacent to the undersurface 19 of the thumb rest 16. A first stiffening web/blade cover 30 extends continuously along a first side of the plastic body 12 from the detent arm 48, past the thumb rest 16 to the resilient spring loop 14. A lancet device setting or resetting notch 32 is optionally provided in the first stiffening web/blade cover 30 to facilitate setting or resetting of the device 10 as will be further explained. A secondary beam deflector post 28 extends toward an upper surface 38 of the blade beam 36 from the under-surface 19 of the thumb rest 16. The thumb rest 16 and the finger rest 22 have respectively textured gripping surfaces 18 and 24, for enhancing the user's grip on the lancet device 10. The thumb rest 16 includes a small protrusion referred to herein as a thumb rest barrier 20. The thumb rest barrier 20 denotes the end of the thumb rest 16 which is closest to the spring loop 14. A similar protrusion referred to herein as a finger barrier 26 is also provided on the finger rest 22. Like the thumb rest barrier 20, the finger barrier 26 denotes the end of finger rest 22 which is closest to the spring loop 14. The thumb rest barrier 20 and the finger barrier 26 facilitate the proper placement of a user's thumb and finger respectively on the thumb rest 16 and the finger rest 22.

Extending from the finger rest 22 in the same direction thereof is an arcuate-shaped incised finger rest 54. The incised finger rest 54 includes an incision port 56 (outline in broken lines) which allows the passage therethrough of the cutting blade 44. A resiliently deflectable beam driver arm 58 extends from the free end of the incised finger rest 54 in the direction of the detent arm 48. The beam driver arm 58 includes an enlarged beam driver member 60 at a free end thereof, which defines a beam driver edge surface 62. The beam driver arm 58 also includes a blade beam stop 64 disposed on the inner surface 59 thereof. The blade beam stop 64 defines a ramp surface 66 which merges with the inner surface 59 of the beam driver arm 58 and a stop surface 68 which is generally perpendicular to the inner surface 59 of the beam driver arm 58. A second stiffening web/blade cover 34 extends continuously along a second side of the plastic body 12 from the beam driver arm 58, past the incised finger rest 54 to the finger rest 22.

The blade beam 36 extending centrally from the inner surface 15 of the spring loop 14, includes upper and lower surfaces 38 and 40 and terminates with an upwardly inclined free end surface 42. The cutting blade 44 is disposed marginally adjacent to the free end surface 42 on the lower surface 40 thereof so that the cutting blade 44 is located over the incision port 56 of the incised finger rest 54. Preferably, the blade 44 is triangular in shape with two sharpened edges 46A and 46B. The cutting blade 44 is a separate metal piece that is molded into the blade beam 36 or otherwise mechanically or adhesively anchored thereto. Alternatively, the cutting blade 44 is a unitary plastic portion of the blade beam 36 as mentioned earlier. The thickness T of the blade beam 36 gradually increases as it extends from the spring loop 14 towards the free end surface 42. This increases the mass of the blade beam 36 in the area of the cutting blade 44 and thus, operates to power the incision and bounce out of the cutting blade 44.

Figure 2:
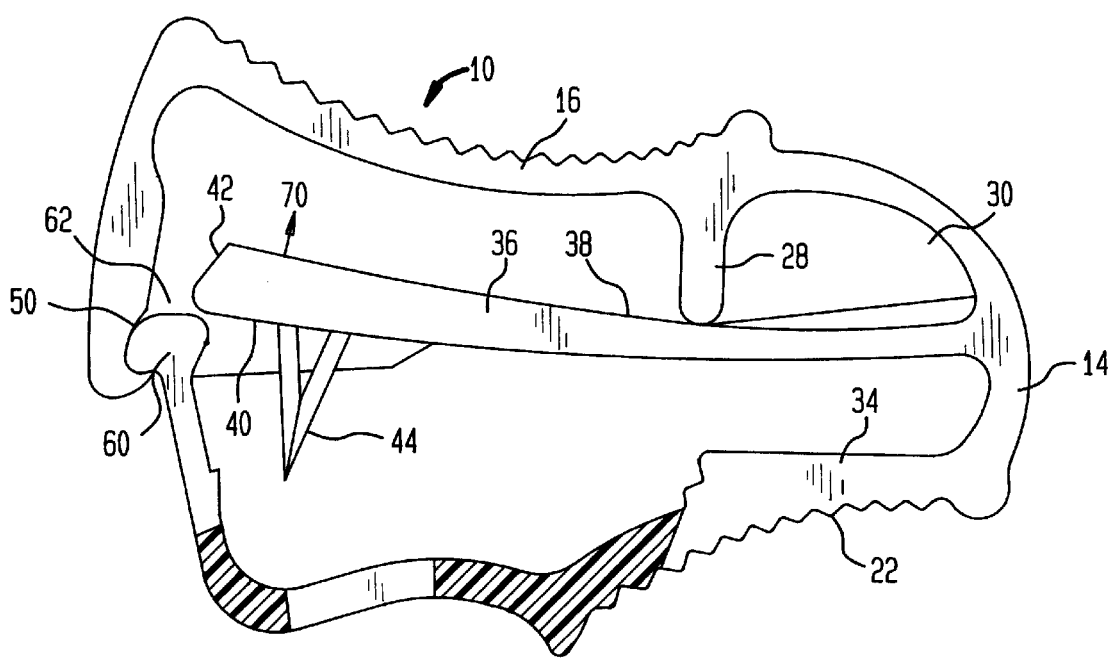
FIG. 2 is a partial cross-sectional side view of the lancet device of the present invention assembled in a ready to use position.

Generally, the lancet device 10 of FIG. 1 is assembled into a ready to use position and packaged in a sterile package (not shown). FIG. 2, is a partial cross-sectional view of the lancet device 10 of FIG. 1 set in the ready to use position after it has been removed from its packaging. In the ready to use position, the secondary beam deflector 28 operates as a pivot by engaging the upper surface 38 of the blade beam 36 while the lower surface 40 of the blade beam 36 immediately adjacent to the inclined surface 42 thereof engages the beam driver edge surface 62 thereby resiliently deflecting the portion of the blade beam 36 wedged between the beam deflector 28 and the beam driver 60 in the direction of arrow 70. In order to maintain the blade beam 36 in the deflected state described above, the beam driver 60 snaps into the detent notch 50. Since the spring loop biases 14 the thumb and finger rests 16 and 22 away from each other, the beam driver 60 remains securely in the detent notch 50. Further, the thumb and finger rests 16 and 22, and the first and second stiffening web/covers 30 and 34 in the ready to use position define an enclosure which keeps the cutting blade 44 sterile and prevents accidental contact with the cutting blade 44.

Figure 3A:
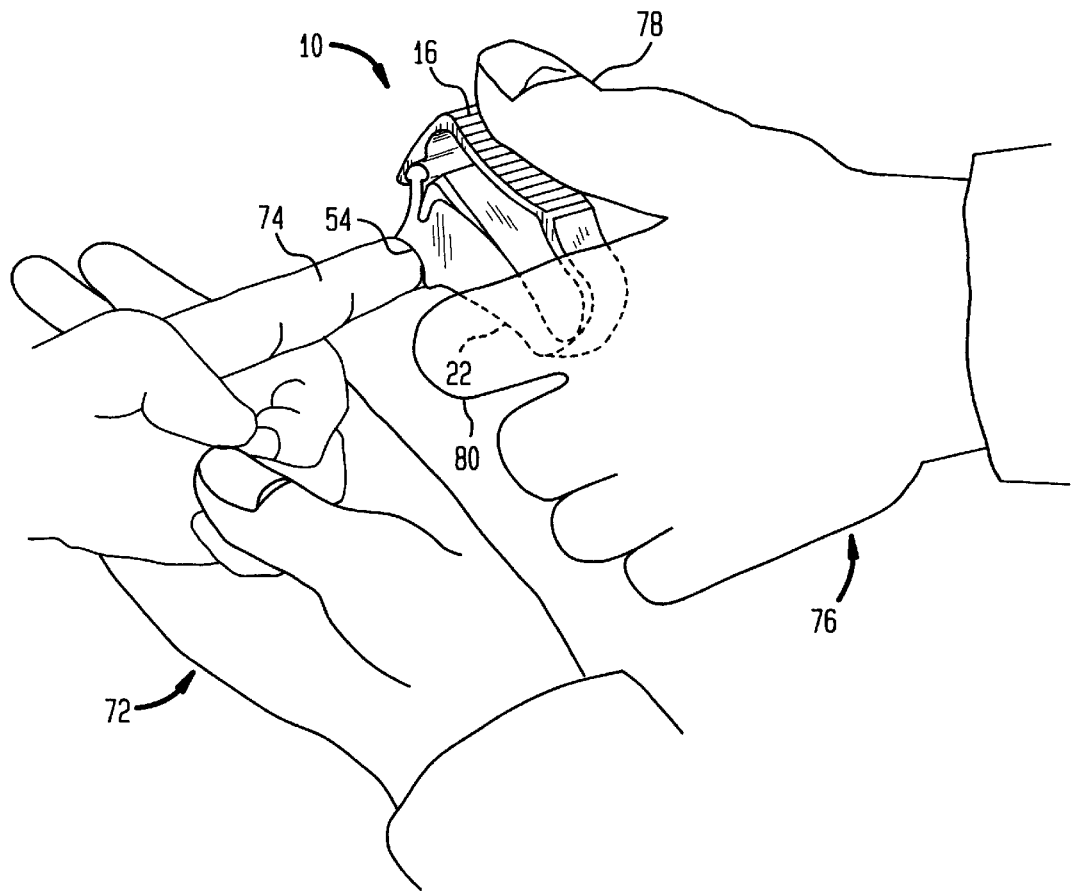
FIG. 3A depicts second person assist use of the lancet device of the present invention on a patient.
Figure 3B:
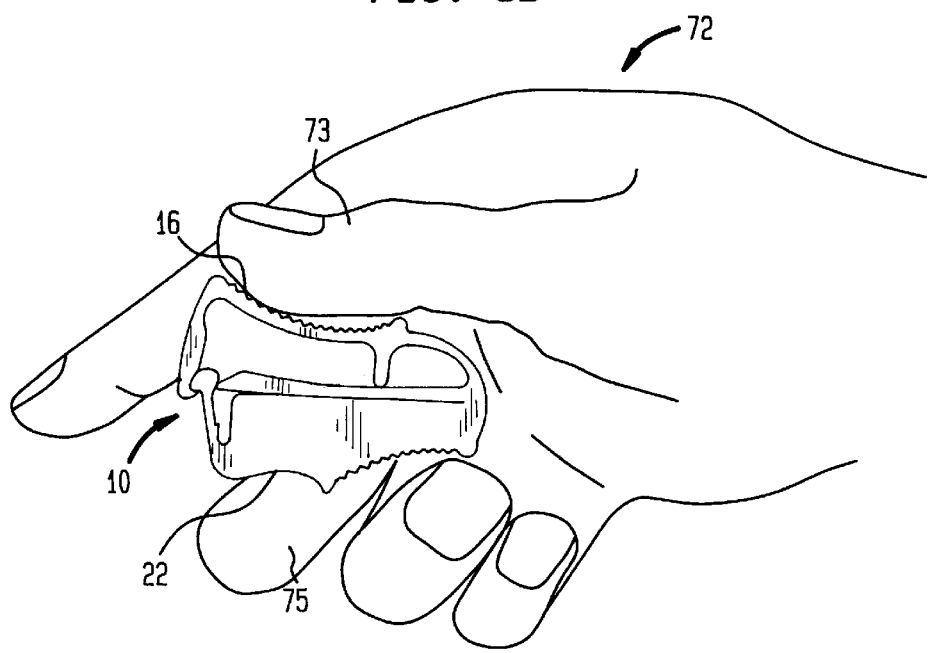
FIG. 3B depicts self use of the lancet device of the present invention.

FIGS. 3A and 3B depict the use of the lancet device 10 of the present invention. In particular, FIG. 3A illustrates second person assist use on a patient 72 wherein a health care worker 76 operates the lancet device for the patient 72. The health care worker 76 positions the incised finger rest 54 of the lancet device 10 on the index finger 74 of the patient 72, grips the lancet device on the thumb rest 16 and finger rest 22 with the thumb 78 and index finger 80 respectively and compresses the lancet device 10 to operate it. FIG. 3B illustrates self use of the lancet device without any second person assistance. For self use, the patient 72 grips the lancet device 10 on the thumb rest 16 and the incised finger rest 22 with the thumb 73 and finger 75 to be incised respectively, and compresses the lancet device 10 to operate it.

Figure 4A:
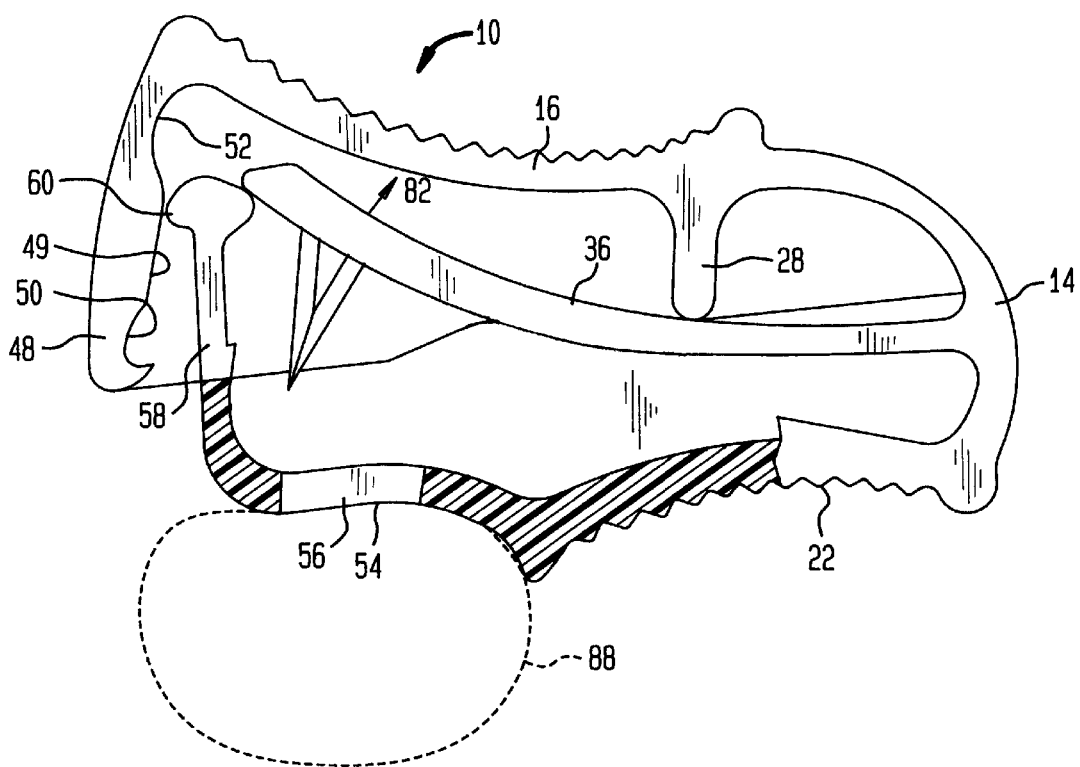
FIGS. 4A–4F are partial cross-sectional side views depicting the operation of the lancet device of the present invention.

FIG. 4A shows the lancet device 10 in a partially compressed position just prior to the release of the blade beam 36. This is accomplished by squeezing the thumb rest 16 and the finger rest 22 toward each other to compress the lancet device 10. Since the beam driver arm 58 is resiliently deflectable, the beam driver arm 58 bends in the direction of arrow 82 to allow the beam driver 60 to disengage from the detent notch 50 and slide along the inner surface 49 of the detent arm 48 toward the beam driver release notch 52. As the beam driver 60 slides toward the beam driver notch 52, the portion of the blade beam 36 wedged between the secondary beam deflector 28 and the beam driver 60 is increasingly deflected in the direction of arrow 84 which results in a buildup of potential energy or a biasing force in the blade beam 36.

Figure 4B:
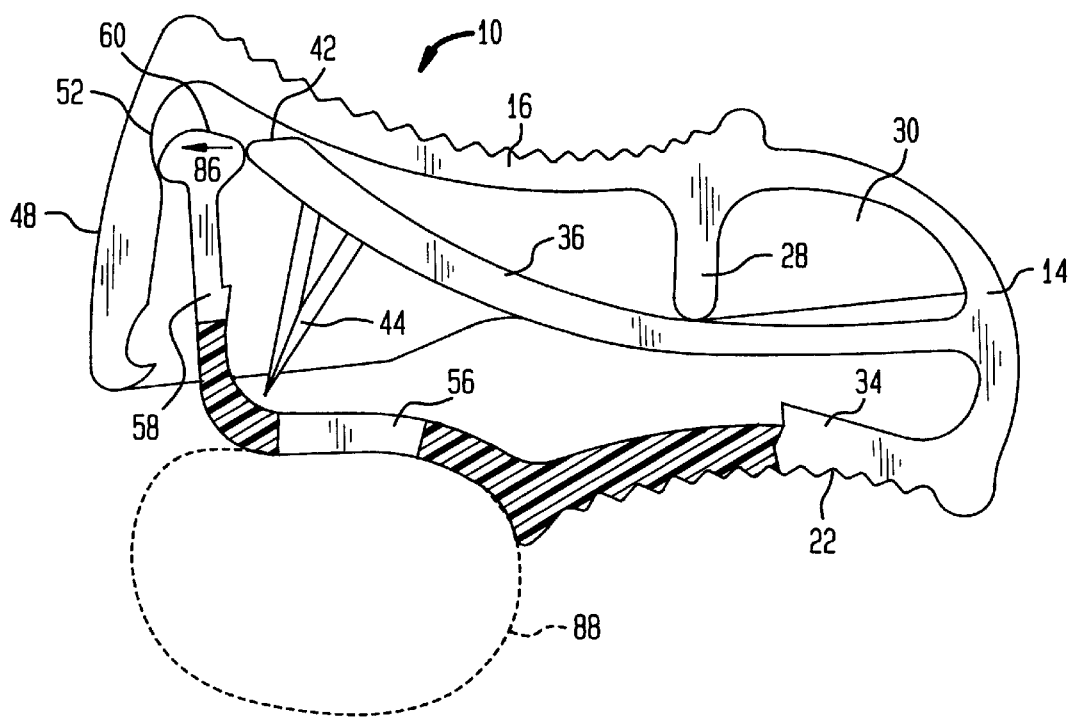
Figure 4C:
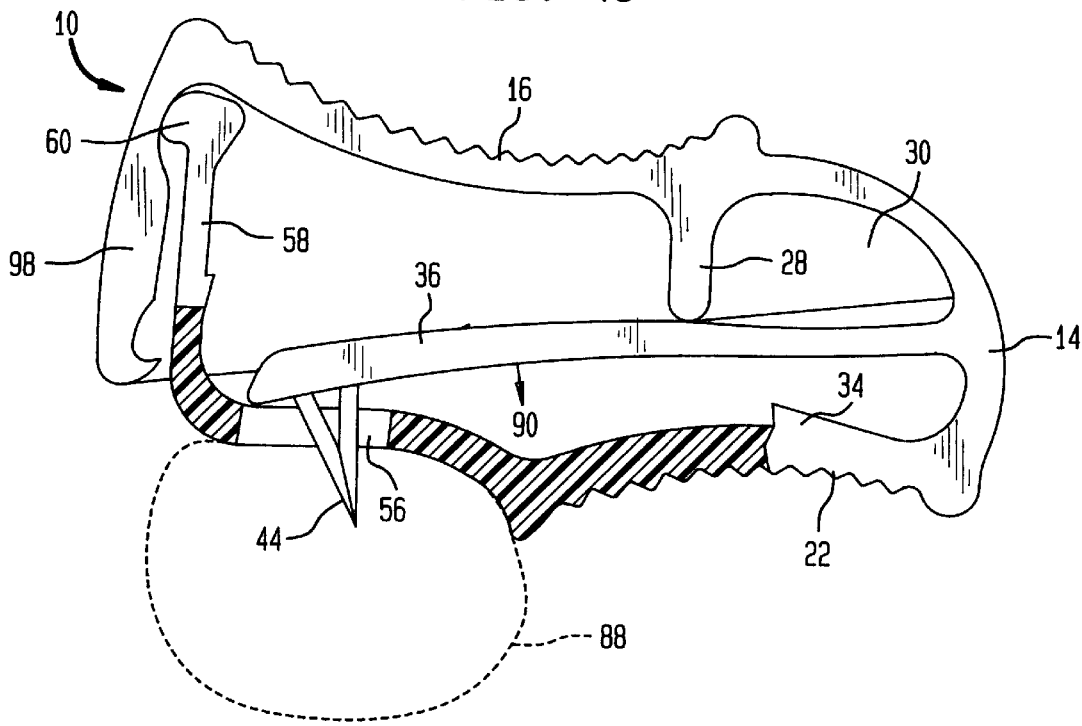

FIG. 4B shows the lancet device 10 in a fully compressed, incision position where the beam driver 60 enters the beam driver notch 52 in the detent arm 48 and thus, allows the beam driver 60 to move away from the blade beam 36 in the direction of arrow 86. As the beam driver 60 moves in the direction of arrow 86, the edge of the blade beam 36 slides off the beam driver 60 thereby releasing the biased blade beam 36. The potential energy stored within the released blade beam 36 accelerates the cutting blade 44 while the increased mass at the blade end of the blade beam 36, power the cutting blade 44 through the incision port 56 and into the skin of the finger to be incised 88 as shown in FIG. 4C. The acceleration and mass of the blade end of the blade beam 36, causes the blade beam 36 to deflect in a second direction indicated by arrow 90.

Figure 4D:
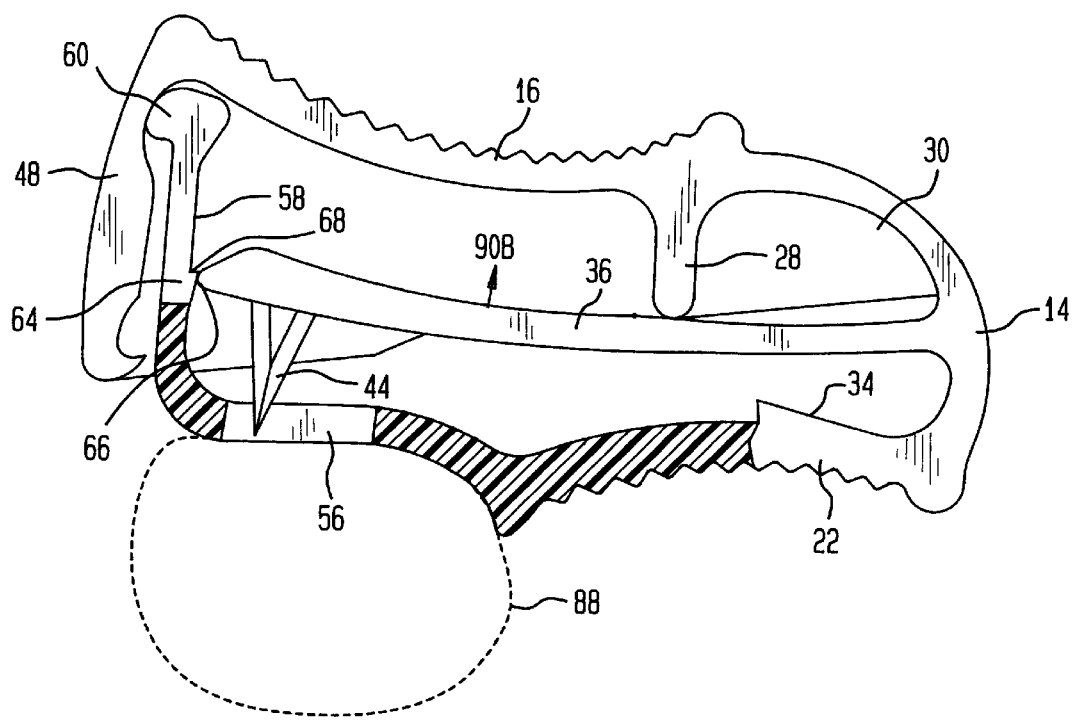
Figure 4E:
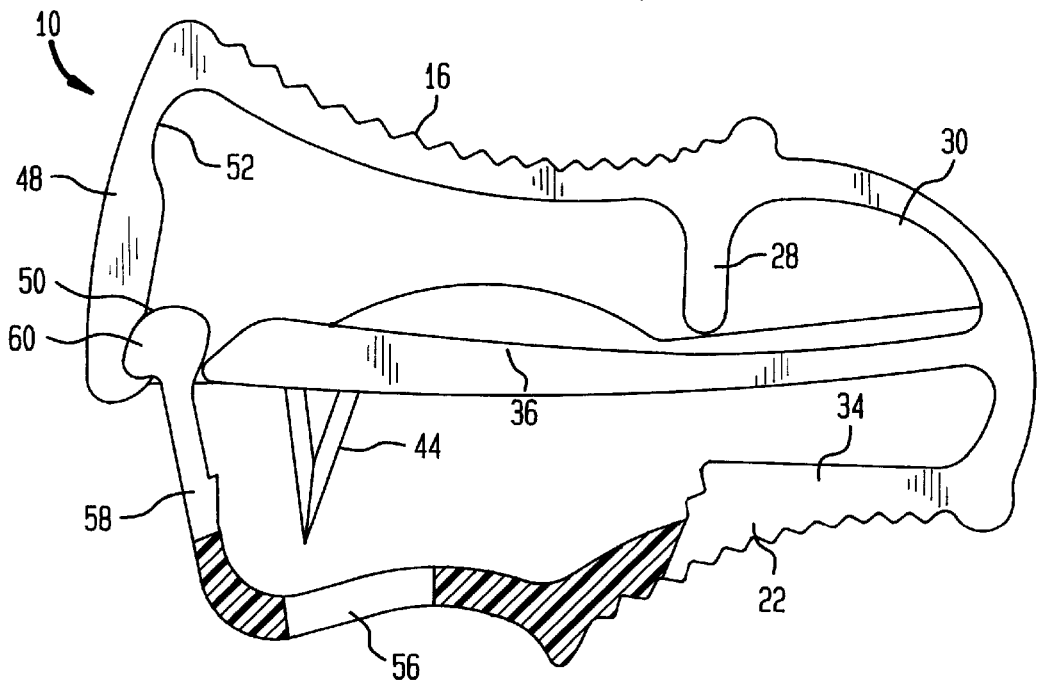
Figure 4F:
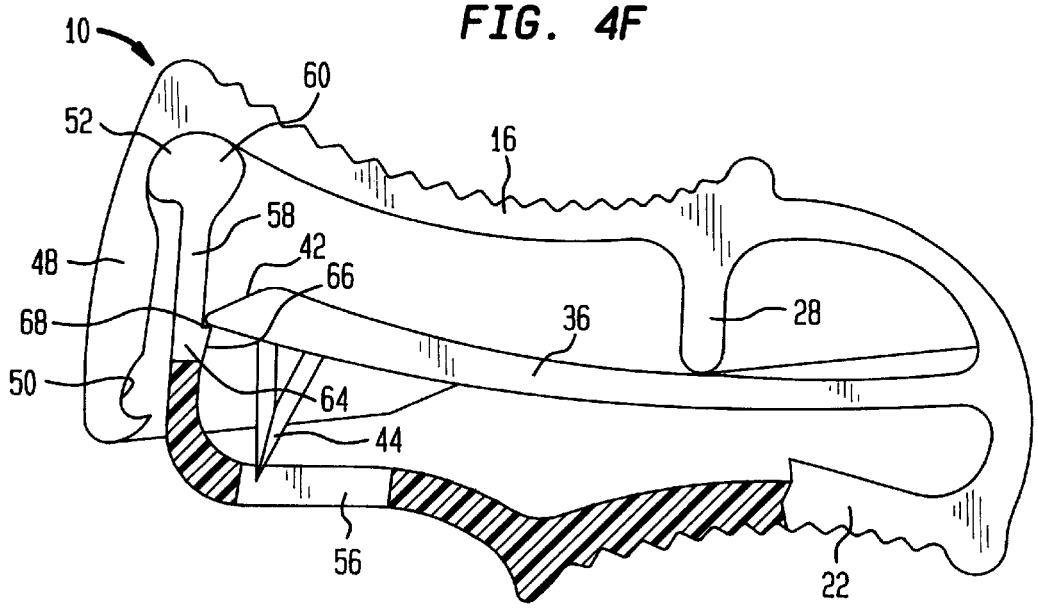

FIG. 4D shows the cutting blade 44 immediately after the blade beam 36 has withdrawn it from the skin and back through the incision port 56. The second deflection of the blade beam 36 buildups enough potential energy to automatically withdraw the cutting blade 44 from the skin, and retract the cutting blade 44 back through the incision port 56 and into the enclosure defined by the thumb and finger rests 16 and 22 and the first and second stiffening web/covers 30 and 34. Thus, moving the beam 36 in direction 90B back to its starting, or rest position. As the user releases the lancet device 10, the spring loop 14 which biases the thumb rest 16 and the finger rest 22 away from each other, expands the lancet device 10 to a discard position. Accordingly, the beam keeper slides 60 out of the beam keeper release notch 52 and returns to the detent notch 50 in the detent arm 48 while at the same time, the inclined surface 42 of the blade beam 36 slides over the inclined surface 66 of the blade beam stop 64. FIG. 4E depicts the lancet device 10 in the discard position where the end of the blade beam 36 rests between the beam keeper 60 and the stop surface 68 of the blade beam stop 64. Accordingly, the cutting blade 44 cannot be forced out of the incision port 56 even if the lancet device 10 is subsequently compressed as shown in FIG. 4F, thus, preventing accidental contact with the cutting blade 44. With the lancet device 10 in the discard position and the cutting blade 44 fully concealed and protected from accidental contact, the lancet device 10 can be discarded in the trash.

If it should be desirable to reuse the lancet device 10 the optionally provided reset notch 32 in the first stiffening web/blade cover 30 (FIG. 1) enables the lancet device 10 to be reset. This is accomplished by first releasing the beam keeper 60 from the detent notch 50. Next, the user's finger is inserted through the reset notch 32 in the first stiffening web/blade cover 30 and placed under the blade beam 36. The user's finger deflects the blade beam 36 up toward the secondary beam deflector 28 while the beam keeper 60 is snapped back into the detent notch 50. When the user releases the blade beam 36 the edge thereof rests on the beam keeper edge surface 62. Accordingly, the lancet device 10 is ready to use again.

It should be understood that the embodiments described herein are merely exemplary and that a person skilled in the art may make many variations and modifications to the disclosed embodiments utilizing functionally equivalent elements to those described herein. Any and all such variations or modifications as well as others which may become apparent to those skilled in the art, are intended to be included within the scope of the invention as defined by the appended claims.

What is claimed is:

1. A safety lancet device, comprising:
   a first arm member;
   a second arm member slidably engaging along said first arm from a first position to a second position when said lancet device is compressed to operate by a user; and
   a pivotally coupled beam member having a cutting blade disposed at an end thereof, said end of said beam member engaging said second arm member in said first position and disengaging said second arm in said second position, wherein said beam member resiliently deflects in a first direction as said second arm moves from said first position to said second position thereby causing a buildup of a biasing force in said beam member, said biasing force causing said beam member to accelerate said cutting blade through an aperture in said lancet device to incise the user's skin when said beam member disengages said second arm in said second position.

2. The safety lancet device according to claim 1, wherein said first arm includes a first notch and said second arm includes notch engaging means for engaging said first notch when said second arm is in said first position.

3. The safety lancet device according to claim 2, wherein said first arm further includes a second notch, said notch engaging means engaging said second notch when said second arm is in said second position.

4. The safety lancet device according to claim 3, wherein said end of said beam member engages said notch engaging means when said second arm moves from said first position towards said second position.

5. The safety lancet device according to claim 4, wherein said end of said beam member slides off said notch engaging means when said notch engaging means enters said second notch in said first arm.

6. The safety lancet device according to claim 1, further comprising spring biasing means for automatically returning said second arm to said first position when said device is released.

7. The safety lancet device according to claim 1, wherein said acceleration of said beam member and said cutting blade causes said beam member to resiliently deflect in a second direction.

8. The safety lancet device according to claim 7, wherein said beam member has an increased mass at said end thereof which operates to resiliently deflect said beam member in said second direction.

9. The safety lancet device according to claim 7, wherein said beam member deflected in said second direction, buildups a second biasing force which causes said beam member to return in a third movement or direction to a non-deflected position thereby withdrawing said cutting blade from the user's skin and back through said aperture.

10. The safety lancet device according to claim 9, wherein said second arm includes stop means for preventing said cutting blade from inadvertently passing through said aperture a second time.

11. The safety lancet device according to claim 10, further comprising means for enabling a user to reposition said beam member on said second arm in order to reuse said safety lancet device.

12. The safety lancet device according to claim 1, wherein said first arm, said second arm, said beam member, and said cutting blade are unitarily molded together to form a single part thereby substantially minimizing the cost of said safety lancet device.

13. The safety lancet device according to claim 12, wherein said first arm, said second arm, and said beam member are made from a plastic material and said cutting blade is made from a metallic material.

14. The safety lancet device according to claim 12, wherein said first arm, said second arm, said beam member, and said cutting blade are made from a plastic material.

15. A safety lancet device, comprising:

a thumb rest;

a finger rest disposed opposite to said thumb rest;

a detent arm coupled to said thumb rest;

a beam keeper arm coupled to said finger rest, said beam keeper arm slidably engaging along said detent arm from a first position to a second position when a user compresses said thumb and finger rest together to operate said lancet device; and a pivotally coupled beam member having a cutting blade disposed at an end thereof, said end of said beam member engaging said beam keeper arm in said first position and disengaging said beam keeper arm in said second position, wherein said beam member resiliently deflects in a first direction as said beam keeper arm moves from said first position to said second position thereby causing a buildup of a biasing force in said beam member, said biasing force causing said beam member to accelerate said cutting blade through said aperture in said lancet device to incise the user's skin when said beam member disengages said beam keeper arm in said second position.

16. The safety lancet device according to claim 15, wherein said detent arm includes a first and second notches and said beam keeper arm includes notch engaging means for engaging said first notch when said beam keeper arm is in said first position and for engaging said second notch when said beam keeper arm is in said second position.

17. The safety lancet device according to claim 16, wherein said end of said beam member engages said notch engaging means when said beam keeper arm moves from said first position towards said second position and slides off said notch engaging means when said notch engaging means enters said second notch in said detent arm.

18. The safety lancet device according to claim 15, further comprising spring biasing means coupling said thumb and finger rests together for automatically expanding apart said thumb and finger rests when said device is release thereby causing said beam keeper arm to return to said first position.

19. The safety lancet device according to claim 15, wherein said beam member has an increased mass at said end thereof which operates to resiliently deflect said beam member in a second direction.

20. The safety lancet device according to claim 19, wherein said beam member deflected in said second direction, buildups a second biasing force which causes said beam member to return to a non-deflected position thereby withdrawing said cutting blade from the user's skin and back through said aperture.

21. The safety lancet device according to claim 20, wherein said beam keeper arm includes stop means for preventing said cutting blade from inadvertently passing through said aperture a second time.

22. The safety lancet device according to claim 15, further comprising:

cover means disposed on first and second sides of said safety lancet device for preventing contact with said cutting blade; and finger access means for enabling a user to reposition said beam member on said beam keeper arm in order to reuse said safety lancet device.

23. A unitarily formed safety lancet device, comprising:

a thumb rest;

a finger disposed opposite to said thumb rest;

a detent arm coupled to said thumb rest;

a beam keeper arm coupled to said finger rest, said beam keeper arm slidably engaging along said detent arm from a first position to a second position when a user compresses said thumb and finger rest together to operate said lancet device;

a pivotally coupled beam member having a cutting blade disposed at an end thereof, said end of said beam member engaging said beam keeper arm in said first position and disengaging said beam keeper arm in said second position, wherein said beam member resiliently deflects in a first direction as said beam keeper arm moves from said first position to said second position thereby causing a buildup of a biasing force in said beam member, said biasing force causing said beam member to accelerate said cutting blade through said aperture in said lancet device to incise the user's skin when said beam member disengages said beam keeper arm in said second position, said acceleration of said beam member and said cutting blade operating to resiliently deflect said beam member in a second direction, building up a second biasing force which causes said beam member to return to a non-deflected position thereby withdrawing said cutting blade from the user's skin and back through said aperture; and cover means disposed on first and second sides of said safety lancet device for preventing contact with said cutting blade.

* * * * *